United States Patent
Chinchoy

(10) Patent No.: US 7,269,460 B2
(45) Date of Patent: Sep. 11, 2007

(54) METHOD AND APPARATUS FOR EVALUATING AND OPTIMIZING VENTRICULAR SYNCHRONIZATION

(75) Inventor: Edward Chinchoy, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 499 days.

(21) Appl. No.: 10/376,980

(22) Filed: Feb. 28, 2003

(65) Prior Publication Data

US 2004/0172077 A1   Sep. 2, 2004

(51) Int. Cl.
 *A61N 1/00* (2006.01)
(52) U.S. Cl. ......................................................... 607/23
(58) Field of Classification Search ............... 607/4–28
 See application file for complete search history.

(56) References Cited

U.S. PATENT DOCUMENTS

| | | | | |
|---|---|---|---|---|
| 4,543,963 | A * | 10/1985 | Gessman | 600/515 |
| 4,995,857 | A | 2/1991 | Arnold | |
| 5,011,380 | A | 4/1991 | Kovacs | |
| 5,129,394 | A | 7/1992 | Mehra | |
| 5,169,381 | A | 12/1992 | Snyders | |
| 5,330,505 | A * | 7/1994 | Cohen | 607/6 |
| 5,564,434 | A | 10/1996 | Halperin et al. | |
| 5,851,227 | A * | 12/1998 | Spehr | 607/126 |
| 6,070,101 | A | 5/2000 | Struble et al. | |
| 6,206,477 | B1 | 3/2001 | Rexus et al. | |
| 6,223,082 | B1 | 4/2001 | Bakels et al. | |
| 6,264,601 | B1 | 7/2001 | Jassawalla et al. | |
| 6,280,389 | B1 | 8/2001 | Ding et al. | |
| 6,309,350 | B1 * | 10/2001 | VanTassel et al. | 600/300 |
| 6,370,427 | B1 * | 4/2002 | Alt et al. | 607/4 |
| 6,443,884 | B1 | 9/2002 | Miyawaki | |
| 6,473,645 | B1 | 10/2002 | Levine | |
| 6,511,413 | B2 * | 1/2003 | Landesberg | 600/17 |
| 6,585,635 | B1 * | 7/2003 | Aldrich | 600/16 |
| 6,666,826 | B2 * | 12/2003 | Salo et al. | 600/485 |

OTHER PUBLICATIONS

Bongiorni, et al., "Is Local Myocardial Contractility Related to Endocardial Acceleration Signals Detected by a Transvenous Pacing Lead?", *PACE*, vol. 19, Nov. 1996, Part II, pp. 1682-1688.

Vogel, et al., "Validation of Myocardial Acceleration During Isovolumic Contraction as a Novel Noninvasive Index of Right Ventricular Contractility Comparison with Ventricular Pressure-Volume Relations in an Animal Model", *Circulation*, Apr. 9, 2002, pp. 1693-1699.

(Continued)

*Primary Examiner*—Scott M. Getzow
(74) *Attorney, Agent, or Firm*—Paul H. McDowall

(57) ABSTRACT

A method and apparatus for determining a metric of cardiac ventricular synchronization and optimizing a cardiac therapy based on the ventricular synchronization metric are provided. A ventricular synchronization metric is determined by: monitoring right and left ventricular pressure; plotting right ventricular pressure as a function of left ventricular pressure to form an RVP-LVP loop; and integrating with respect to direction to determine an area of the RVP-LVP loop which, according to one convention, is mathematically negative during left ventricular led pressure development and is mathematically positive during right ventricular led pressure development. Timing parameters used to control the delivery of cardiac resynchronization therapy or ventricular assist device therapy are adjusted as needed according to the ventricular synchronization metric.

27 Claims, 10 Drawing Sheets

OTHER PUBLICATIONS

Bordachar, et al., "Hemodynamic Assessment of Right, Left, and Biventricular Pacing by Peak Endocardial Acceleration and Echocardiography in Patients with End-Stage Heart Failure", *PACE*, vol. 23, Nov. 2000, Part II, pp. 7126-1730.

Padeletti, et al., "Atrioventricular Interval Optimization in the Right Atrial Appendage and Interatrial Septum Pacing: A Comparison Between Echo and Peak Endocardial Acceleration Measurements", *PACE*, vol. 23, Nov. 2000, Part I, pp. 1618-1622.

Plicchi, et al., "PEA I and PEA II based implantable haemodynamic monitor: pre clinical studies in sheep", *Europace*, 2002, vol. 4, pp. 49-54.

Rickards, et al., "An Implantable Intracardiac Accelerometer for Monitoring Myocardial Contractility", *PACE*, Dec. 1996, Part I, vol. 19, pp. 2066-2071.

Leung, et al., "Automatic Optimization of Resting and Exercise Atrioventricular Interval Using a Peak Endocardial Acceleration Sensor: Validation with Doppler Echocardiography and Direct Cardiac Output Measurements", *PACE*, Nov. 2000, Part II, vol. 23, pp. 1762-1766.

\* cited by examiner

METHOD AND APPARATUS FOR EVALUATING AND OPTIMIZING VENTRICULAR SYNCHRONIZATION

FIELD OF THE INVENTION

The present invention relates generally to medical devices for treating or monitoring mechanical cardiac dysfunction and more particularly to a device and method for assessing and optimizing right and left ventricular synchronization.

BACKGROUND OF THE INVENTION

Evaluation of left ventricular function is of interest for both diagnostic and therapeutic applications. During normal cardiac function, the left atrium, the left ventricle, and the right ventricle observe consistent time-dependent relationships during the systolic (contractile) phase and the diastolic (relaxation) phase of the cardiac cycle. During cardiac dysfunction associated with pathological conditions or following cardiac-related surgical procedures, these time-dependent mechanical relationships are often altered. This alteration, when combined with the effects of weakened cardiac muscles, reduces the ability of the ventricle to generate contractile strength resulting in hemodynamic insufficiency. A method for quantifying the degree of ventricular asynchrony would be useful for both diagnostic purposes and in selecting and optimizing a therapy to restore ventricular synchrony.

Ventricular dyssynchrony following coronary artery bypass graft (CABG) surgery is a problem encountered relatively often, requiring postoperative temporary pacing. Atrio-biventricular pacing has been found to improve postoperative hemodynamics following such procedures. A widely accepted, standardized method for selecting pacing sites and pacing intervals that provide the greatest hemodynamic benefit to the patient during the critical recovery phase, however, has not been available.

Chronic ventricular resynchronization therapy has been clinically demonstrated to improve indices of cardiac function in patients suffering from congestive heart failure. Cardiac pacing may be applied to one or both ventricles or multiple heart chambers, including one or both atria, to improve cardiac chamber coordination, which in turn is thought to improve cardiac output and pumping efficiency. Clinical follow-up of patients undergoing resynchronization therapy has shown improvements in hemodynamic measures of cardiac function, left ventricular volumes, and wall motion. However, not all patients respond favorably to cardiac resynchronization therapy. Physicians are challenged in selecting patients that will benefit and in selecting the optimal pacing intervals applied to resynchronize the heart chamber contractions.

Selection of pacing parameters may be based on echocardiographic studies performed to determine the settings resulting in the best hemodynamic response. Significant hemodynamic changes may not always be acutely observable in an individual patient using non-invasive monitoring methods. Selection of parameters may therefore be based on avoidance of altered or impeded ventricular filling. In the MIRACLE clinical trial conducted to evaluate resynchronization therapy, the A-V interval was optimized individually in patients by shortening the A-V interval to maximize LV filling without truncating the atrial contribution as observed by echocardiography.

Doppler tissue imaging has been used clinically to investigate coordination between septal and lateral wall motion and has been proposed as a method for predicting which patients are likely to benefit from resynchronization therapy. Evidence suggests patient response is dependent on the degree of ventricular synchrony before and after therapy.

Echocardiographic approaches, however, provide only an open-loop method for selecting pacing intervals. After evaluating the hemodynamic effect of varying combinations of pacing intervals, a physician must manually select and program the desired parameters and assume that the patient's device optimal settings remain unchanged until a subsequent re-optimization visit. Furthermore, an echocardiographic procedure for optimizing resynchronization therapy can require substantial time and personnel. An automated method for selecting pacing intervals during resynchronization therapy is therefore desirable.

Multichamber pacing systems having automated selection of pacing intervals have been proposed. A four-chamber pacing system that includes impedance sensing for determining the timing of right heart valve closure or right ventricular contraction and adjusting the timing of delivery of left ventricular pace pulses is generally disclosed in U.S. Pat. No. 6,223,082 issued to Bakels, et al., incorporated herein by reference in its entirety. Programmable coupling intervals selected so as to provide optimal hemodynamic benefit to the patient in an implantable multichamber cardiac stimulation device are generally disclosed in U.S. Pat. No. 6,473,645 issued to Levine, incorporated herein by reference in its entirety.

It would be desirable to provide a method for automatically optimizing a resynchronization therapy based on a parameter indicative of ventricular synchrony. Evaluation of hemodynamic or electrocardiographic (ECG) parameters may be used in assessing ventricular synchrony. QRS width is generally considered to widen with ventricular asynchrony. However, measurement of QRS width is typically not a sensitive measure for indicating improvements in ventricular synchrony. Direct analysis of right and left ventricular pressure waveforms is another method of assessing ventricular synchrony. Comparison of rapid pressure changes in the left and right ventricles during systole, however, becomes problematic due to limited time resolution. One approach to eliminating a time resolution limitation is to evaluate right ventricular pressure as a function of left ventricular pressure, or, conversely, left ventricular pressure as a function of right ventricular pressure. A method and apparatus for determining whether a heart failure patient will benefit from pacing therapy involving calculating the area associated with an RVP versus LVP loop is generally disclosed in U.S. Pat. No. 6,280,389 issued to Ding et al., incorporated herein by reference in its entirety.

In experimental studies performed by the inventor of the present invention, integration of the RVP-LVP loop did not differentiate between normal and heart failure subjects unless the integration method took into account the direction of the RVP-LVP loop pathway, resulting in a vector having a mathematically positive or negative value. Furthermore, unless a direction-dependent method of integration was used, the resulting RVP-LVP loop area was dependent on heart rate. A parameter for assessing ventricular synchrony should be independent of heart rate.

Other options for treating a heart failure patient include ventricular assist devices (VADs). End-stage heart failure patients may be implanted with a left ventricular assist device (LVAD) while awaiting a heart transplant.

Heart failure patients undergoing surgery may also be provided with an LVAD to acutely unload the ventricle to promote recovery. A major problem faced by physicians, however, is that 20% to 30% of patients treated with an LVAD develop right ventricular failure that is refractory to medical treatment. Right ventricular function may decline as a result of changes to right ventricular preload and after load resulting from abnormal pressure imbalances between the left and right ventricle as well as abnormal wall movement observed as septal shifting and free wall asynchronous bulging. Maintaining a greater degree of synchrony between right and left ventricular pressure development may prevent the demise of right ventricular function in the presence of an LVAD.

From the above discussion, it is apparent that, in the evaluation of heart failure patients for therapy selection, in the evaluation of therapy effectiveness, and in improving the understanding of heart failure and heart failure therapy mechanisms, a reliable metric of ventricular synchronization is needed. Such a metric would be useful in optimizing resynchronization therapy delivery or VAD operation. A reliable metric should be independent of heart rate and dependent on heart failure. Furthermore, such a metric preferably distinguishes between left-led and right-led ventricular pressure development such that resynchronization therapy or VAD operation may be adjusted appropriately for restoring ventricular synchrony and promoting myocardial recovery.

SUMMARY OF THE INVENTION

The present invention is directed toward providing a method and apparatus for determining a reliable metric of ventricular synchronization and optimizing a heart failure therapy or cardiac pacing therapy based on the ventricular synchronization metric. The synchronization metric is preferably based on the relationship of right ventricular pressure (RVP) plotted as a function of left ventricular pressure (LVP). Accordingly, the present invention includes measuring the RVP and LVP, or correlates thereof, for a desired time interval; plotting RVP as a function of LVP; integrating to determine the area enclosed by the RVP-LVP plot wherein the integration method takes into account the direction in which the RVP-LVP loop is plotted, which will generally be a clockwise or counter-clockwise direction. The resulting area advantageously allows right ventricular led pressure development, which will be mathematically positive, to be distinguished from left ventricular led pressure development, which will be mathematically negative. A metric of synchronization may thus be defined as the average area enclosed by an RVP-LVP loop per cardiac cycle. This average RVP-LVP loop area can be normalized by the average area bounded by the maximum and minimum RVP and LVP occurring during each cardiac cycle.

The synchronization metric will be useful in optimizing cardiac resynchronization therapy or the operation of a ventricular assist device (VAD). In one embodiment of the present invention, a multi-chamber cardiac pacemaker is modified to include RVP and LVP sensing capabilities and data processing for determining a synchronization metric from RVP and LVP data. Timing parameters controlling the delivery of right ventricular and left ventricular pacing pulses may be adjusted automatically or manually based on the synchronization metric.

In another embodiment, an external system for monitoring ventricular synchronization based on analysis of RVP-LVP loops is provided. Such an external system is useful for bedside, postoperative monitoring of cardiac surgery patients. The external system may include a therapy delivery system, which in one embodiment is a temporary pacing system for treating post-operative cardiac dysynchrony. The need for temporary pacing as well as appropriate pacing intervals are determined by evaluating a synchronization metric derived from the RVP-LVP loop data.

In yet another embodiment, a heart failure therapy system includes a VAD and a cardiac monitor/stimulator capable of determining a ventricular synchronization metric based on the RVP-LVP loops. Timing parameters controlling the actuation of the VAD and/or timing parameters controlling pacing pulse delivery to the opposite, unassisted ventricle may be adjusted automatically or manually in order to achieve a normal, or near-normal, synchronization metric.

DETAILED DESCRIPTION OF THE INVENTION

The present invention provides a method for assessing and optimizing ventricular synchronization. Time-dependent hemodynamic parameters related to cardiac events in the two ventricles, namely right ventricular pressure (RVP) and left ventricular pressure (LVP) or correlates thereof, are used to quantify ventricular synchronization by determining a metric based on a mathematical relationship of RVP and LVP or correlates thereof. This assessment of ventricular function is useful in either an acute or chronic setting. Possible applications of the methods described herein, therefore, include, but are not limited to, patient monitoring, acute or chronic pacing therapy, acute or chronic hemodynamic loading or unloading, and acute or chronic drug delivery.

Figure 1:
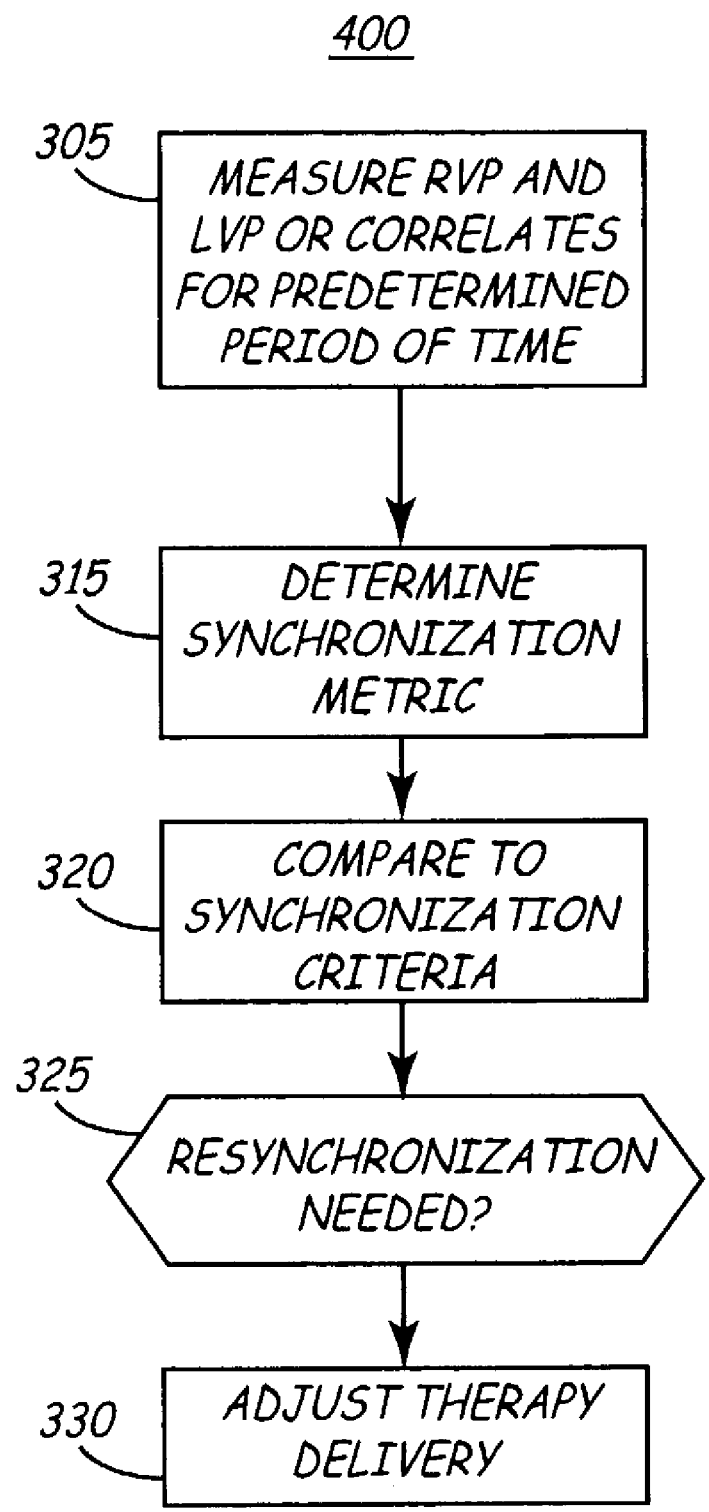
FIG. 1 is a flow chart providing an overview of a method provided by the present invention for determining a metric of ventricular synchronization and using this metric for optimizing the delivery of a heart failure therapy.

FIG. 1 is a flow chart providing an overview of a method provided by the present invention for determining a metric of ventricular synchronization and using this metric for optimizing the delivery of a heart failure therapy. At step 305, right and left ventricular pressures, or correlates thereof, are measured continuously for a predetermined period of time or a desired number of cardiac cycles. Right and left ventricular pressure may be measured directly by placing a pressure transducer in each ventricle. While the right ventricle is relatively accessible for direct pressure measurement, through a venous access site, the left ventricle is generally not easily accessed for direct pressure measurement. Therefore, alternative embodiments may include the measurement of a correlate of left ventricular pressure in place of direct left ventricular pressure measurement. Correlates of LVP may be derived from measurements made based on accelerometer sensors, sonomicrometry crystals, flow transducers, acoustical or optical sensors, etc.

At step 315, a metric of ventricular synchronization is calculated based on the measured RVP and LVP or correlates thereof. Methods for calculating a ventricular synchronization metric will be described in greater detail in conjunction with FIG. 2. At step 320, the determined metric is compared to predefined synchronization criteria. Such criteria, which may be tailored according to individual patient need, defines a threshold or range that specifies values associated with normal ventricular synchronization. If the calculated metric falls outside this normal range, resynchronization is indicated as determined at decision step 325. A heart failure or resynchronization therapy is adjusted at step 330 until the synchronization metric is acceptably improved. Adjustment of a therapy may involve resetting escape intervals for ventricular, biventricular, dual chamber or multichamber pacing, delivering right ventricular pacing at a desired interval relative to left ventricular cardiac assist device (LVAD) ejection, or adjusting the timing of LVAD ejection. Adjustment of a therapy may alternatively involve a prescribed change in a medical therapy.

Figure 2:
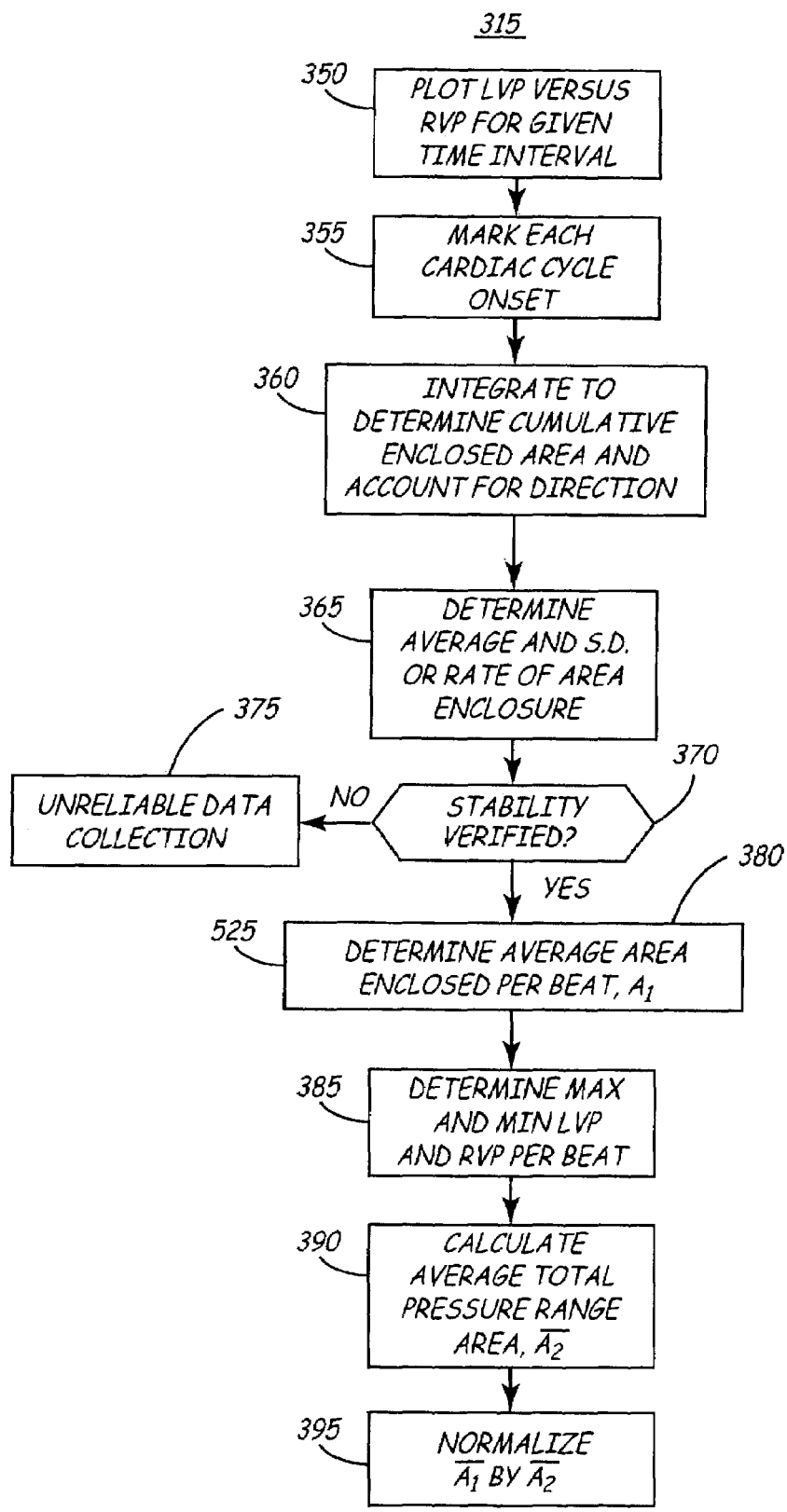
FIG. 2 is a flow chart detailing a method for calculating a metric of ventricular synchronization based on right and left ventricular pressure measurement, for use in the method of FIG. 1.

FIG. 2 is a flow chart detailing a method for calculating a metric of ventricular synchronization based on right and left ventricular pressure measurement, for use in the method 300 of FIG. 1. At step 350, measured RVP is plotted as a function of measured LVP, or a correlate thereof, for a given time interval, for example on the order of 30 seconds. As indicated above, RVP and LVP are measured continuously such that an RVP-LVP loop may be plotted for each cardiac cycle. RVP and LVP signals received from a pressure sensor or other sensor provided for measuring a correlate of RVP and LVP are preferably sampled simultaneously at equal rates. An acceptable sampling rate is on the order of 250 Hz. However, lower sampling rates may be adequate. The RVP-LVP loop is generated by plotting the simultaneously sampled RVP and LVP points. The RVP-LVP loop allows the relationship between left and right ventricular systolic pressure development and diastolic pressure decline to be directly evaluated.

In alternative embodiments, a subset of the points defining an RVP-LVP loop may be sampled and stored. For example, RVP and LVP signals or correlates thereof may be sampled during a particular interval of the cardiac cycle or predetermined fiducial points may be selected and stored.

During RVP and LVP data acquisition, the onset of each cardiac cycle is preferably marked at step 355. Cardiac cycle onset may be detected based on a threshold pressure measurement differentiating the end of diastole and the onset of systole. Alternatively, cardiac cycle onset may be indicated based on sensing of a P-wave or R-wave on an ECG or EGM signal.

At step 360, the cumulative area enclosed by the RVP-LVP loop during the monitoring interval is determined by integration. A ventricular synchronization metric preferably distinguishes between a right-leading ventricular sequence of pressure development and a left-leading ventricular sequence. This distinction allows a therapy to be adjusted in the proper manner to restore ventricular synchrony. As such, the method of integration used to determine the cumulative area at step 360 preferably takes into account the direction of RVP-LVP loop enclosure. One suitable method of integration that accounts for the direction of enclosure is based on Green's theorem.

Figure 3A:
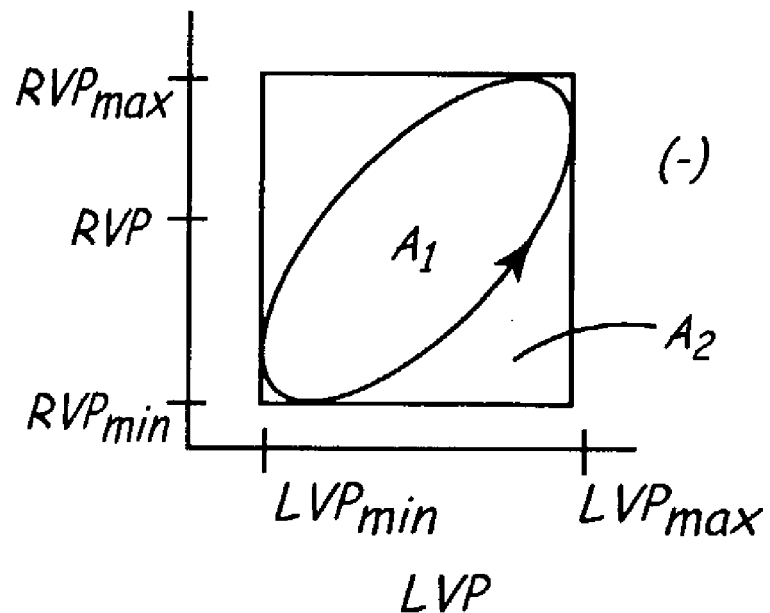
FIG. 3A is a hypothetical graph of right ventricular pressure plotted as a function of left ventricular pressure in which left ventricular pressure development precedes right ventricular pressure development resulting in an area enclosed in a generally counter-clockwise direction.
Figure 3B:
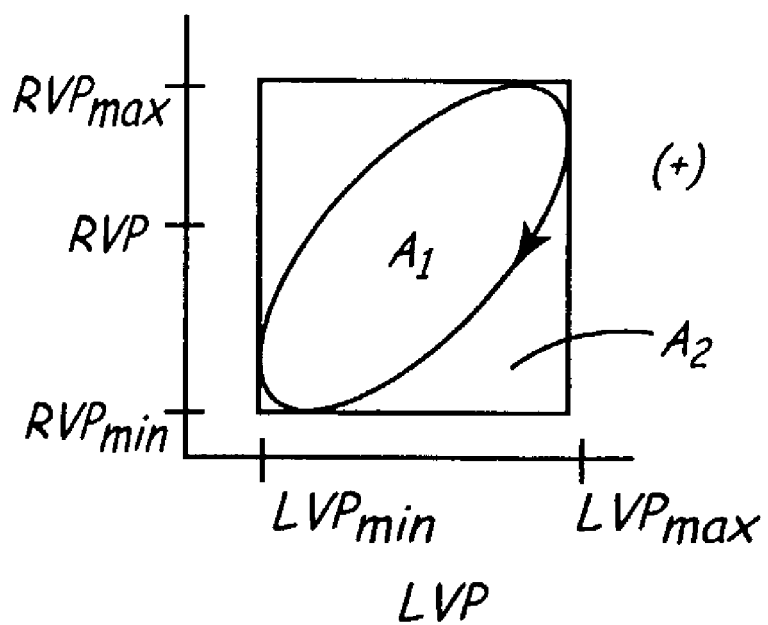
FIG. 3B is a hypothetical graph of right ventricular pressure plotted as a function of left ventricular pressure in which right ventricular pressure development precedes left ventricular pressure development resulting in an area enclosed in a generally clockwise direction.

FIGS. 3A and 3B are hypothetical graphs of right ventricular pressure plotted as a function of left ventricular pressure. In FIG. 3A, left ventricular pressure development precedes right ventricular pressure development resulting in an area enclosed in a counter-clockwise direction, as indicated by the arrow, when RVP is plotted as a function of LVP. The enclosed area, labeled as $A_1$, calculated according to Green's theorem is mathematically negative by convention. In FIG. 3B, right ventricular pressure development precedes left ventricular pressure development resulting in an area enclosed in a clockwise direction, as indicated by the arrow, when RVP is plotted as a function of LVP. The area calculated according to Green's theorem is mathematically positive. This distinction allows right-leading ventricular asynchrony to be distinguished from left-leading ventricular asynchrony.

Figure 4A:
FIG. 4A is a sample graph of an RVP-LVP loop as may be expected during normal sinus rhythm.
Figure 4B:
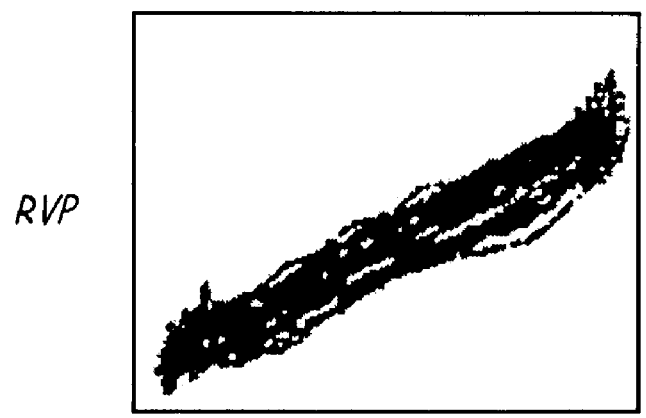
FIG. 4B is a sample graph of an RVP-LVP loop as may be expected during heart failure.

FIG. 4A is a sample graph of an RVP-LVP loop as may be expected during normal sinus rhythm. The loop is relatively smooth and regular. FIG. 4B is a sample graph of an RVP-LVP loop as may be expected during heart failure. The plot is irregular and may self-intersect resulting in both clockwise-enclosed portions and counter-clockwise enclosed portions. The total area calculated in this situation is a net area since integration of generally counter-clockwise portions will be mathematically negative and generally clockwise portions will be mathematically positive.

After calculating the cumulative area enclosed by the RVP-LVP loops at step 360 of FIG. 2, the rate of area enclosure and its average and standard deviation are determined at step 365. The rate of area enclosure, defined as the time derivative of the cumulative area enclosed, is preferably stable, indicating a stable heart rate, during RVP and LVP data acquisition. Anomalous data can result in the presence of ectopic heart beats or other rate abnormalities. Therefore a minimum period of time, for example on the order of 10 seconds, during which the rate of enclosure is stable is desired for determining a ventricular synchronization metric.

Rate stability may be verified at step 370 by comparing the standard deviation of the average rate of enclosure to a maximum allowable standard deviation. If stability is not verified, the data is deemed unreliable for determining a ventricular synchronization metric. If stability is verified, the area enclosed per cardiac cycle is determined at step 380.

In one embodiment, the average area enclosed per cardiac cycle, referred to herein as "$\overline{A}_1$," is determined by dividing the cumulative area enclosed by the RVP-LVP loop during a stable monitoring time interval, T, by the number of cardiac cycles (CC) during the monitoring time. The cumulative area may be equivalently expressed as the summation of the RVP-LVP loop areas integrated for each cardiac cycle during the time interval T as shown in the following equation used for calculating $\overline{A}_1$:

significantly with heart rate within the control group or within the heart failure group. However, at each heart rate tested, $\overline{A}_1$ and $\overline{A}_1/\overline{A}_2$ were significantly different between the control and HF groups. The normalized average area of the RVP-LVP loop per cardiac cycle, $\overline{A}_1/\overline{A}_2$, was found to be on the order of −0.3 in the normal subjects, regardless of heart rate. Thus, heart failure could be distinguished from normal, regardless of heart rate based on these synchronization metrics. The results are set forth in the table below:

|  | $\overline{A}_1$ | | | $\overline{A}_1/\overline{A}_2$ | | |
|  | NSR | 120 bpm | 180 bpm | NSR | 120 bpm | 180 bpm |
| --- | --- | --- | --- | --- | --- | --- |
| Control | −508 ± 81 | −567 ± 112 | −549 ± 152 | −0.3 ± 0.07 | −0.32 ± 0.05 | −0.32 ± 0.1 |
| HF | −10 ± 304 | −28 ± 297 | 22 ± 461 | 0.0 ± 0.18 | −0.01 ± 0.18 | 0.0 ± 0.26 |

$$\overline{A}_1 = \frac{\sum_{i=0}^{i=T} \left( \int RVP(LVP) \right)_i}{CC}$$

At step 385, the maximum and minimum LVP and maximum and minimum RVP are determined for each cardiac cycle. At step 390, the average area of the total pressure range, referred to herein as "$\overline{A}_2$," is calculated. In FIGS. 3A and 3B, the area enclosed by an RVP-LVP loop is labeled as $A_1$. The total pressure range area, labeled as $A_2$, is shown bounded by the minimum and maximum LVP and minimum and maximum RVP that occurred during the given cardiac cycle. The area $A_2$ is calculated according to the following equation:

$$A_2 = (RVP_{max} - RVP_{min}) \times (LVP_{max} - LVP_{min})$$

The average total pressure range area, $\overline{A}_2$, is calculated at step 385 as the summation of the total pressure range areas calculated for each cardiac cycle divided by the number of cardiac cycles, CC, during the monitoring interval, T:

$$\overline{A}_2 = \frac{\sum_{i=0}^{i=T} A_2}{CC}$$

A normalized average area enclosed by the RVP-LVP loop per cardiac cycle may then be calculated by dividing $\overline{A}_1$ by $\overline{A}_2$ at step 395. The average area per cardiac cycle, $\overline{A}_1$, or the normalized average area per cardiac cycle, $\overline{A}_1/\overline{A}_2$, can be used as a metric for assessing ventricular synchrony in method 300 of FIG. 1. These metrics are independent of heart rate, discern between left and right-leading ventricular asynchrony, and distinguish between ventricular synchronization during normal sinus rhythm and heart failure.

In experimental studies, the inventor of the present invention has determined the synchronization metrics $\overline{A}_1$ and $\overline{A}_1/\overline{A}_2$ according to the steps summarized in FIG. 2 described above. RVP-LVP loops were obtained in normal canine subjects (control) and canine subjects induced with heart failure (HF). RVP-LVP loops were obtained at the subject normal sinus rhythm (NSR) and at elevated, pacing-induced rates of 120 bpm and 180 bpm. Neither $\overline{A}_1$ nor $\overline{A}_1/\overline{A}_2$ varied Those skilled in the art will appreciate that the methods described above for determining a ventricular synchronization metric may be incorporated into an implantable monitoring/cardiac stimulation device modified to include direct or surrogate RVP and LVP sensing capabilities. Pressure data may be collected and stored in the implanted device and uplinked via conventional telemetry methods to an external device for processing and analysis. A treating clinician may then review the results to assess ventricular synchrony and make changes to a prescribed therapy accordingly. Alternatively pressure data may be processed directly by the implantable device to allow automatic adjustment of cardiac stimulation parameters such that ventricular synchronization is improved based on the direct assessment of ventricular synchrony according to the synchronization metric described above. Repeated assessment of ventricular synchronization allows re-evaluation of the therapy effectiveness and re-adjustments as necessary.

Accordingly, an embodiment of the present invention is disclosed in detail in the context of a multi-chamber pacing system provided with the capacity to collect and store pressure data and process data, or transfer data to another implanted or external device for processing, for determining a metric of ventricular synchronization. This embodiment of the invention may be programmed to operate as an AV sequential, bi-atrial and/or bi-ventricular pacing system operating in demand, atrial tracking, and triggered pacing mode for restoring synchrony between the left and right heart chambers. This embodiment is therefore programmable to operate as a two, three or four channel pacing system having an AV synchronous operation mode for restoring upper and lower heart chamber synchronization and right and left atrial and ventricular chamber synchronization. However, it will be understood that certain components of the complex multi-chamber pacing system described below can be selectively programmed to be enabled or disabled. Furthermore, it is recognized that device features may be incorporated in a simpler, two-chamber monitoring/stimulation system.

Figure 5:
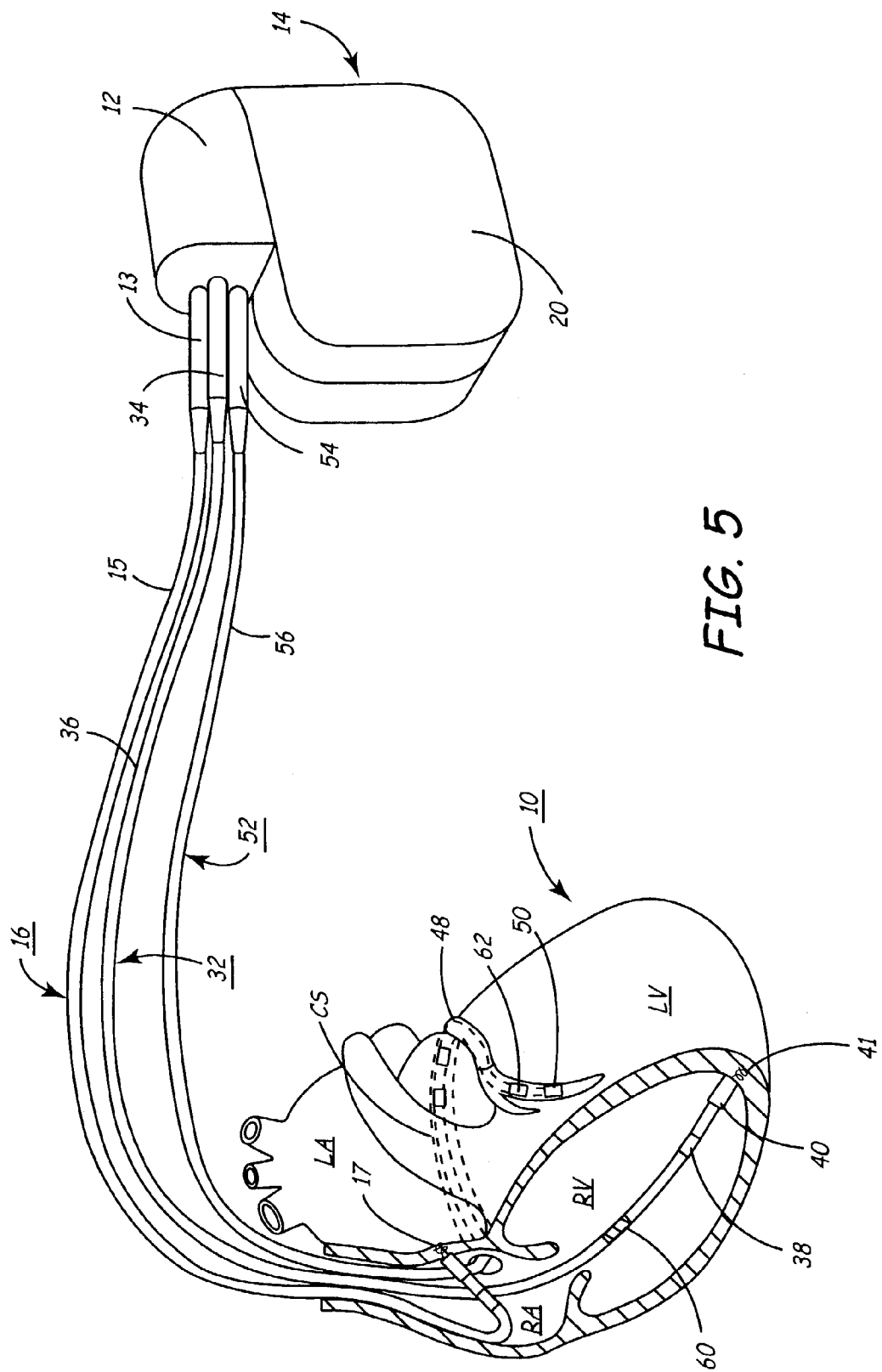
FIG. 5 depicts an implantable, multi-chamber cardiac pacemaker for monitoring and restoring ventricular synchrony coupled to a patient's heart.

In FIG. 5, an implantable, multi-chamber cardiac pacemaker 14 for monitoring and restoring ventricular synchrony is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) extending from the opening in the right atrium laterally around the atria to form the great cardiac vein 48, which branches to form inferior cardiac veins. The pacemaker 14, also referred to herein as the "implantable pulse generator" or "IPG," is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions. The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21 provided for achieving RA pacing and sensing of RA electrogram (EGM) signals.

Bipolar, endocardial RV lead 32 is passed through the RA into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38 provided for RV pacing and sensing of RV EGM signals.

In this illustrated embodiment, a unipolar, endocardial LV CS lead 52 is passed through the RA, into the CS and further into a cardiac vein to extend the distal LV CS pace/sense electrode 50 alongside the LV chamber to achieve LV pacing and sensing of LV EGM signals. The LV CS lead 52 is coupled at the proximal end connector 54 fitting into a bore of IPG connector block 12. A small diameter unipolar lead body 56 is selected in order to lodge the distal LV CS pace/sense electrode 50 deeply in a vein branching from the great vein 48.

In a four chamber embodiment, LV CS lead 52 could bear a proximal LA CS pace/sense electrode positioned along the lead body to lie in the larger diameter coronary sinus adjacent the LA for use in pacing the LA or sensing LA EGM signals. In that case, the lead body 56 would encase an insulated lead conductors extending proximally from the more proximal LA CS pace/sense electrode(s) and terminating in a bipolar connector 54.

In order to provide right ventricular pressure monitoring, the RV lead 32 preferably carries a pressure sensor 60 for measuring developing systolic and diastolic pressures. Accordingly, lead 32 may include a sensor of the type disclosed in U.S. Pat. No. 5,564,434 issued to Halperin, et al., incorporated herein by reference in its entirety, which generally discloses a cardiac lead including a capacitive blood pressure sensor. Because the left ventricular chamber is difficult to access directly for chronic, ambulatory monitoring of LVP, a correlate measure of LVP that is more easily acquired may be monitored in place of direct LVP monitoring. In the illustrated embodiment, CS LV lead 52 is provided with a sensor 62 for monitoring a correlate of LVP. Lead 52 may be of the type described in U.S. Pat. No. 5,129,394 issued to Mehra, incorporated herein by reference in its entirety, which generally discloses a lead with a pressure sensor near its distal end for measuring a pressure in an acutely occluded coronary vein that is proportional to the left ventricular pressure. U.S. Pat. No. 6,206,477 to Miesel et al. entitled, "chronically implantable blood vessel cuff with sensor" discloses a system that may also be used in conjunction with the present invention. This patent to Miesel et al. is incorporated herein in its entirety. Additional conductors carried within lead bodies 36 and 56 carry signals received by pressure sensors 60 and 62 to IPG 14 via connectors 34 and 54.

It is recognized that alternative types of sensors and sensor locations may be substituted for monitoring RVP and LVP or correlates thereof. For example, direct LVP monitoring may be feasible using a pressure sensor introduced into the left ventricle through a septal or epicardial puncture. A pressure monitoring device adapted to be placed in the ventricular septum to permit measurement of pressure in the left ventricle is generally disclosed in U.S. Pat. No. 6,309,350 issued to VanTassel, et al., incorporated herein by reference in its entirety.

Figure 6:
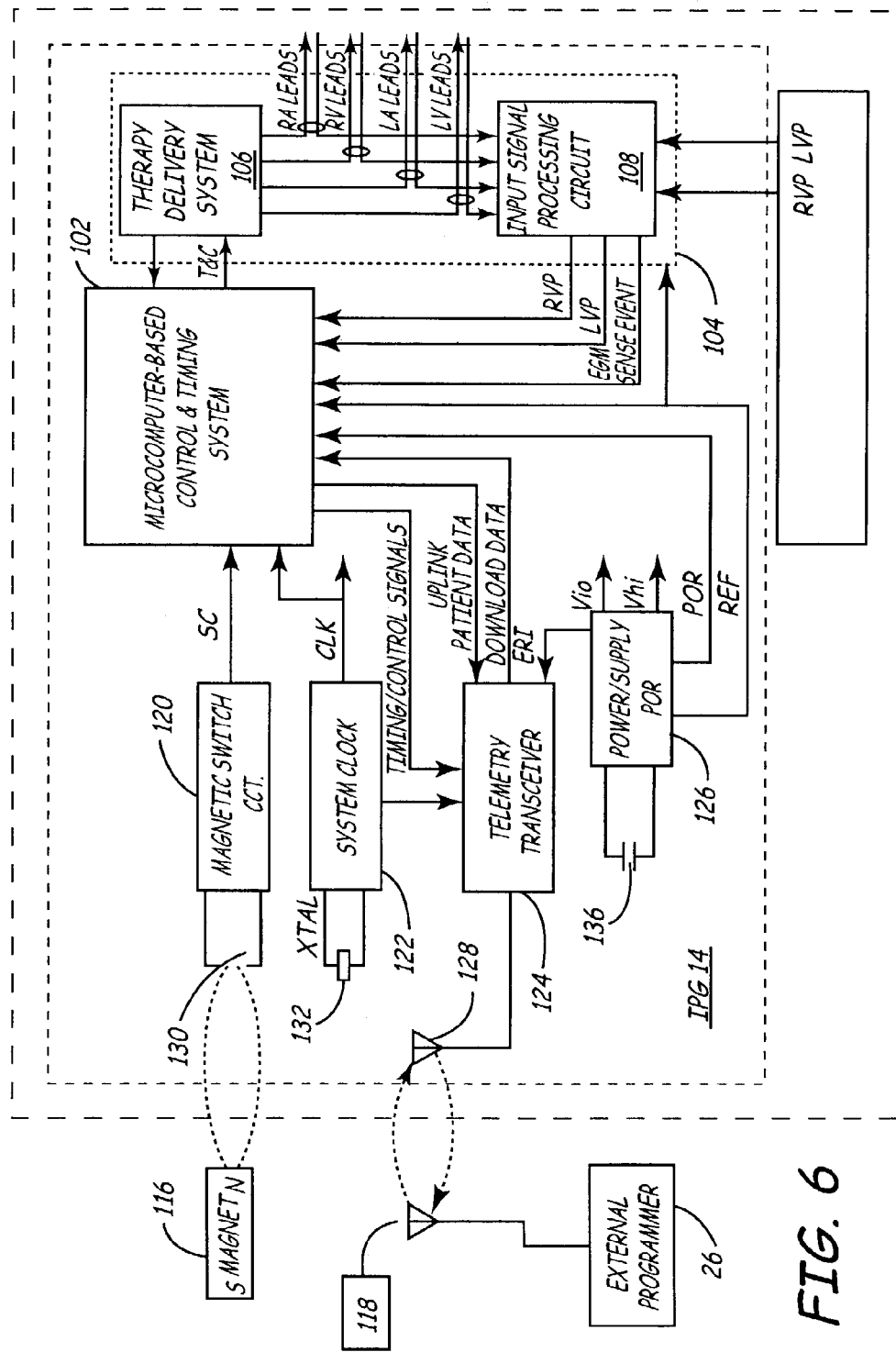
FIG. 6 is a schematic block diagram of the exemplary multi-chamber pacemaker of FIG. 5.

FIG. 6 is a schematic block diagram of the exemplary multi-chamber IPG 14 of FIG. 5 that provides delivery of a resynchronization therapy and is capable of processing physiological signal input. The IPG 14 is preferably a microprocessor-based device. Accordingly, microprocessor-based control and timing system 102, which varies in sophistication and complexity depending upon the type and functional features incorporated therein, controls the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac pacing to control the patient's heart rhythm and resynchronize heart chamber activation. The interface circuitry 104 therefore includes a therapy delivery system 106 intended for delivering cardiac pacing impulses under the control of control and timing system 102. Physiologic input signal processing circuit 108 is provided for receiving cardiac electrogram (EGM) signals for determining a patient's heart rhythm. Physiologic input signal processing circuit 108 additionally receives RVP and LVP signals or correlates thereof, and processes these signals or provides signal data to control and timing system 102 for signal processing. For purposes of illustration of the possible uses of the invention, a set of lead connections are depicted for making electrical connections between the therapy delivery system 106 and the input signal processing circuit 108 and sets of pace/sense electrodes and pressure sensors or other sensors located in operative relation to the RA, LA, RV and LV.

Control and timing system 102 controls the delivery of bi-atrial, bi-ventricular, or multi-chamber cardiac pacing pulses at selected intervals intended to improve heart chamber synchrony. The delivery of pacing pulses by IPG 14 may be provided according to programmable timing intervals, such as programmable conduction delay window times as generally disclosed in U.S. Pat. No. 6,070,101 issued to Struble et al., incorporated herein by reference in its entirety, or programmable coupling intervals as generally disclosed in above-cited U.S. Pat. No. 6,473,645 issued to Levine. Selection of the programmable timing intervals is preferably based on a determination of the synchronization metric described herein. Periodic adjustment of timing intervals may be made automatically or manually based on the determination of the synchronization metric.

The therapy delivery system 106 can optionally be configured to include circuitry for delivering cardioversion/defibrillation therapy in addition to cardiac pacing pulses for controlling a patient's heart rhythm. Accordingly, leads in communication with the patient's heart could additionally include high-voltage cardioversion or defibrillation shock electrodes. In one embodiment, as will be described further below, therapy delivery system 106 may be provided to operate a ventricular assist device or blood pump implanted in patients awaiting a heart transplant operation.

A battery provides a source of electrical energy to power components and circuitry of IPG 14 and provide electrical stimulation energy for delivery electrical impulses to the heart. The typical energy source is a high energy density, low voltage battery 136 coupled with a power supply/POR circuit 126 having power-on-reset (POR) capability. The power supply/POR circuit 126 provides one or more low voltage power Vlo, the POR signal, one or more VREF sources, current sources, an elective replacement indicator (ERI) signal, and, in the case of a cardioversion/defibrillator capabilities, high voltage power Vhi to the therapy delivery system 106. Not all of the conventional interconnections of these voltages and signals are shown in FIG. 6.

Virtually all current electronic multi-chamber monitor/sensor circuitry employ clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 6, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, sensed RVP and LVP signals or correlates thereof, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data may be stored on a triggered or periodic basis or by detection logic within the physiologic input signal processing circuit 108 upon satisfaction of certain predetermined event detection criteria. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic episode data when the patient experiences certain symptoms. In either case, event related data, e.g., the date and time, may be stored along with the stored periodically collected or patient initiated physiologic data for uplink telemetry in a later interrogation session.

Uplink and downlink telemetry capabilities are provided to enable communication with either a remotely located external medical device or a more proximal medical device on or in the patient's body. Stored EGM, or pressure-related data of the types described above as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemetering both analog and digital data between antenna 128 and an external device 26, also equipped with an antenna 118, may be accomplished using numerous types of telemetry systems known in the art for use in implantable devices.

The physiologic input signal processing circuit 108 therefore includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a P-wave or R-wave, respectively and providing an ASENSE or VSENSE event signal to the control and timing system 102. Timing and control system 102 responds in accordance with its particular operating system to deliver or modify a pacing therapy, if appropriate, or to accumulate data for uplink telemetry transmission in a variety of ways known in the art.

Figure 7:
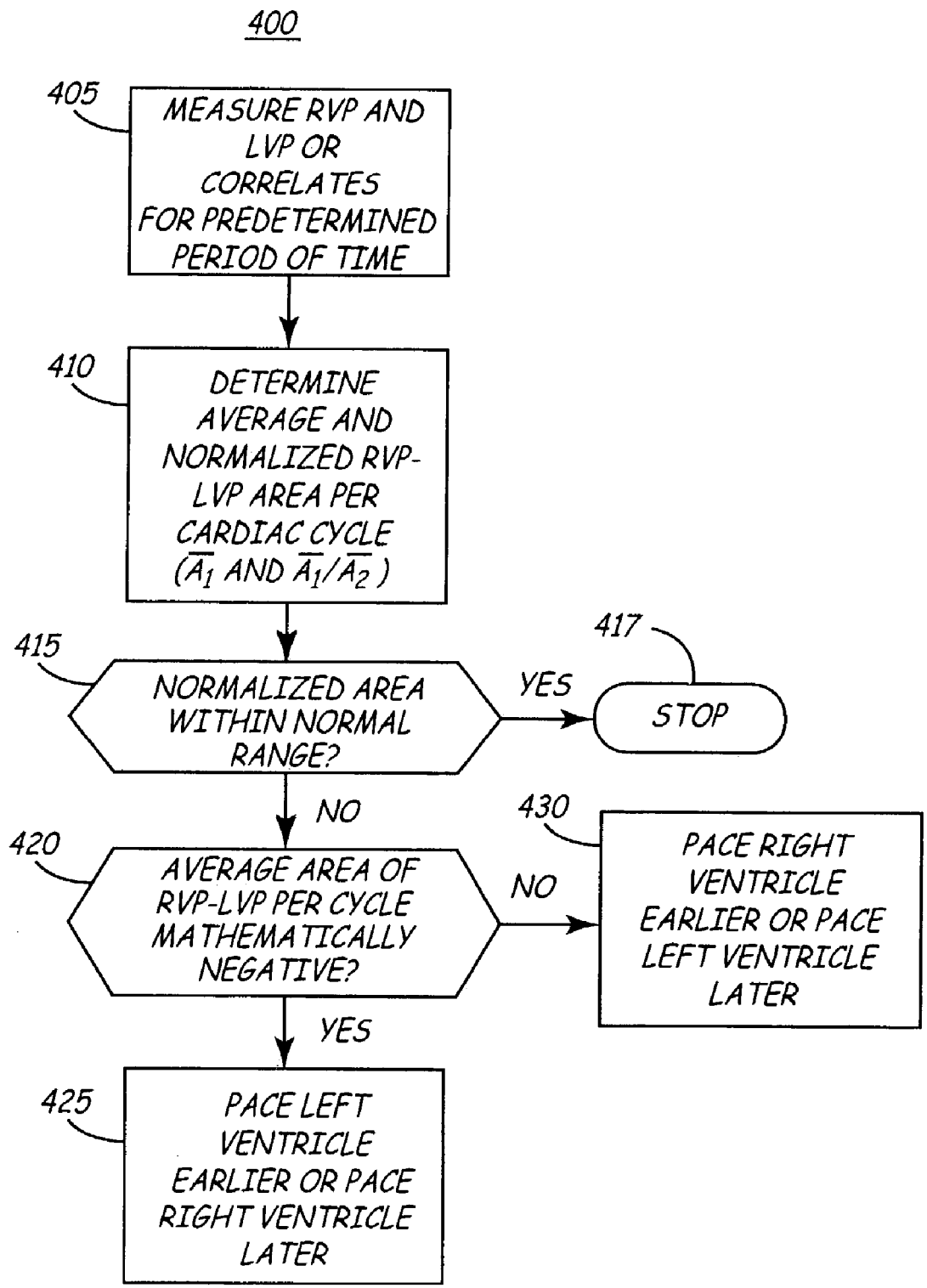
FIG. 7 is a flow chart summarizing the steps included in a method for optimizing ventricular resynchronization therapy using a metric based on RVP and LVP measurements for use in conjunction with the type of device shown in FIG. 6.

FIG. 7 is a flow chart summarizing the steps included in a method for optimizing ventricular resynchronization therapy using a metric based on RVP and LVP measurements for use in conjunction with the type of device described above. At step 405, RVP and LVP, or correlates thereof, are simultaneously measured as described previously. At step 410, a ventricular synchronization metric is determined based on the RVP-LVP relationship. In a preferred embodiment, the average area enclosed per cardiac cycle by the RVP-LVP plot, referred to above as $\overline{A}_1$, is calculated and normalized by the average area of the RVP and LVP range per cardiac cycle, referred to above as $\overline{A}_2$. Either the average area, $\overline{A}_1$, or the normalized area, $\overline{A}_1/\overline{A}_2$, may then be compared to a predetermined normal range associated with normal ventricular synchrony. For example, the inventors of the present invention have found normal ventricular synchrony to result in a value of approximately −500 to −550 mmHg$^2$ for $\overline{A}_1$, and −0.3 for the normalized area $\overline{A}_1/\overline{A}_2$ in experimental studies. If the metric falls at or near the expected normal value, the method 400 may be terminated at step 417. No adjustment to the current resynchronization therapy is needed.

If the synchronization metric does not meet the normal synchronization criterion at decision step 415, the method 400 determines which ventricle is leading in pressure development. As explained previously, by taking into account the direction of the plotted RVP-LVP relationship during integration, the resulting area will be mathematically negative or mathematically positive. A mathematically negative area indicates that pressure development in the right ventricle lags pressure development in the left ventricle. In this case, an adjustment to the timing parameters controlling delivery of right and left ventricular pacing pulses during biventricular pacing is made at step 425 to effectively pace the left ventricle later and/or the right ventricle earlier in the cardiac cycle to restore more normal ventricular synchrony.

If the average area enclosed by the RVP-LVP relationship is mathematically positive, then the pressure developed in the left ventricle lags the pressure developed in the right ventricle. In this case, method 400 will adjust the pacing timing parameters at step 430 such that the right ventricle is paced later and/or the left ventricle is paced earlier in the cardiac cycle.

While method 400 has been described in the context of bi-ventricular pacing, it is recognized that method 400 may be applied in bi-atrial or multi-chamber pacing wherein the timing intervals that determine the depolarization of the left and right ventricles, either via direct pacing or via conduction from the atria, may be adjusted based on the synchronization metric. Furthermore, it is contemplated that a patient determined to have left-led ventricular asynchrony, such as a patient having right bundle branch block, may benefit from adjusting and delivering pacing only in the right atrium and/or right ventricle. Likewise, a patient determined to have right-led ventricular asynchrony, such as a patient having left bundle branch block, may benefit from adjusting and delivering pacing only in the left atrium and/or left ventricle.

Figure 8:
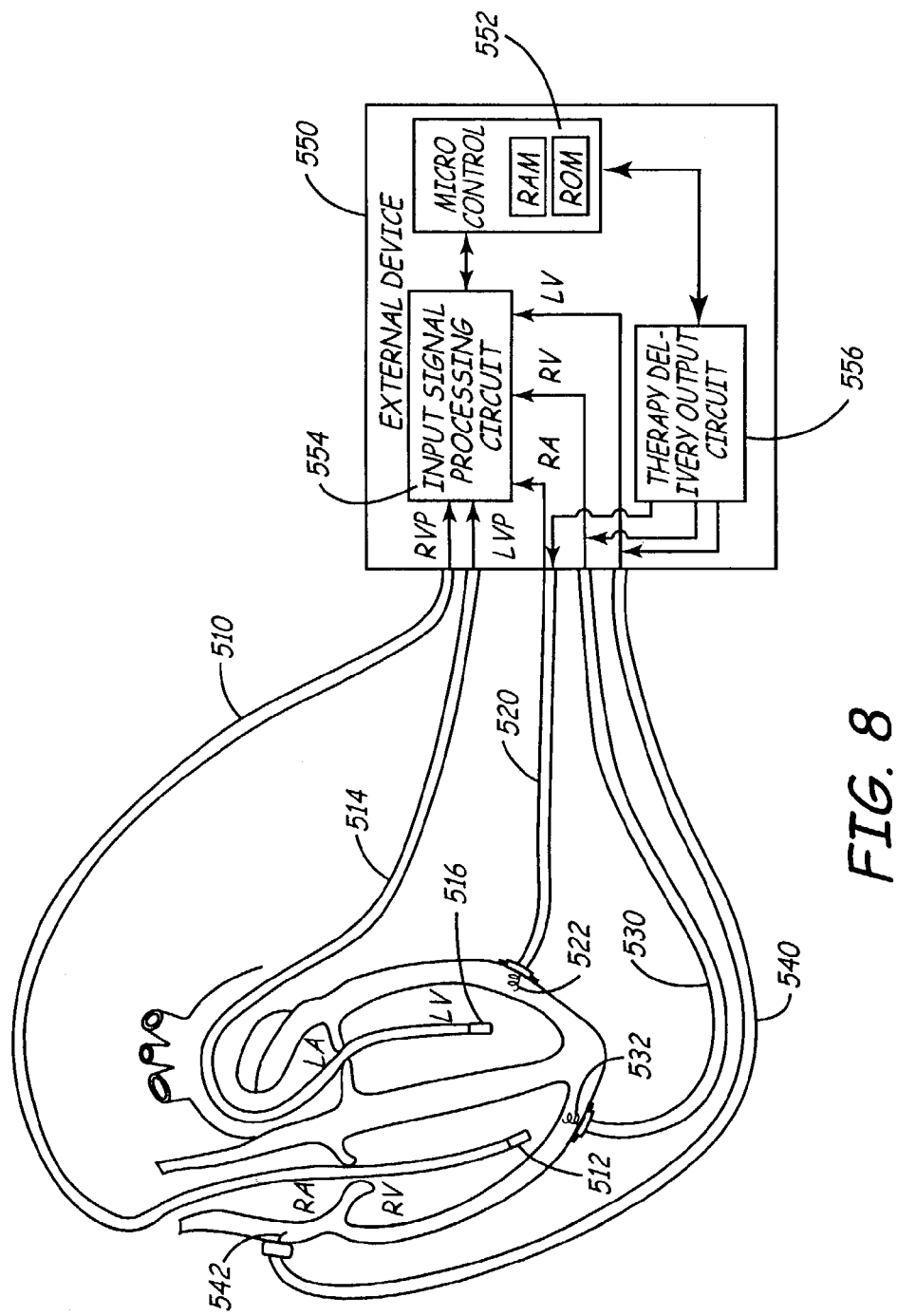
FIG. 8 is a schematic diagram of an external system for monitoring ventricular synchrony based on right and left ventricular pressure signal inputs, or correlates thereof, and delivering a temporary pacing therapy as needed to restore ventricular synchrony.

FIG. 8 is a schematic diagram of an external system for monitoring ventricular synchrony based on right and left ventricular pressure signal inputs, or correlates thereof, and delivering a temporary pacing therapy as needed to restore ventricular synchrony. Aberrant conduction patterns present following cardiac-related surgical procedures can result in hemodynamic compromise due to ventricular dyssynchrony. The external system shown in FIG. 8 is useful for post-operative bedside monitoring of ventricular synchrony.

External device 550 includes input signal processing circuit 554 for receiving a RVP signal and a LVP signal or correlates thereof. In the embodiment shown, RVP and LVP signals are received from pressure sensors placed directly in the respective ventricles. An RV pressure catheter 510 including a pressure sensor 512 is positioned in the RV and provides a RVP signal to input circuit 554. A LV pressure catheter 514 including a pressure sensor 516 is positioned in the LV and provides a LVP signal to input circuit 554. Pressure catheters 512 and 514 may be placed during the process of a surgical procedure and remain implanted during an acute postoperative recovery phase in order to monitor ventricular synchronization. In alternative embodiments, RVP and/or LVP input lines of device 550 are coupled to surrogate invasive or non-invasive sensors capable of generating signals correlated to the respective RVP and/or LVP.

External device 550 is preferably a microprocessor-based device, which may be a personal computer. As such, microcontroller 552, with associated RAM and ROM, is capable of executing programs designed to determine a metric of ventricular synchronization from RVP and LVP data received from input circuit 554 as well as control other device functions. A ventricular synchronization metric is preferably determined according to method 315 of FIG. 2 based on points or a subset of points defining the RVP-LVP loop.

In the embodiment shown in FIG. 8, epicardial leads 520, 530 and 540 are provided for sensing and pacing in the left ventricle, right ventricle, and right atrium, respectively. Right atrial lead 540, right ventricular lead 530, and left ventricular lead 520 are each provided with a respective pace/sense electrode 542, 532 and 522, which are shown as active fixation electrodes. To provide unipolar pacing or sensing, a subcutaneous indifferent electrode (not shown) may also be provided. In alternative epicardial lead systems, additional epicardial leads may be deployed to achieve bipolar pacing and/or sensing in one or more heart chambers. Other types of epicardial or temporary lead systems may be substituted for the particular system shown in FIG. 8 for use with an external pacing system.

Input signal processing circuit 554 receives input from right atrial, right ventricular, and left ventricular pace/sense electrodes 542, 532 and 522. Atrial and ventricular sense signals are sent to microcontroller 552. Pacing pulses are delivered to the appropriate pace/sense electrode(s) 542, 532 or 522 by therapy delivery output circuit 556 under the control of microcontroller 552 according to the selected pacing modality. The need for atrio-biventricular, biventricular, dual chamber, or single chamber pacing and the relative intervals at which pacing is delivered in one or more heart chambers with respect to sensed or paced events in other heart chambers is determined by evaluating ventricular synchrony based on the RVP-LVP relation. Cardiac pacing may be triggered by detection of ventricular dyssynchrony based on analysis of the RVP-LVP relation. Pacing intervals can then be adjusted as needed in order to restore ventricular synchrony according to the methods described previously.

Those skilled in the art will further appreciate that the methods described herein for monitoring and optimizing ventricular synchronization may alternatively be implemented in conjunction with a ventricular assist device. A left ventricular assist device (LVAD) implanted to provide left ventricular unloading may be operated under the control of timing parameters set based on a metric of ventricular synchronization so as to avoid anomalous septal wall motion or ventricular free wall motion (e.g., bulging). Alternatively, the right ventricle could optionally be paced under the control of timing parameters adjusted to optimize a synchronization metric during LVAD operation. Accordingly, a pressure sensor may be provided within the LVAD or the conduit between the LV and LVAD as long as the pressure sensor is exposed to LVP without the interference of a valve that may be included in the conduit, or placed directly into the LV. Additionally, a pressure sensor is placed in the RV. The measured LVP and RVP signals may be received for storage and processing by an implantable IPG, such as the multi-chamber cardiac pacing and monitoring device described above, or a simpler single chamber, bi-ventricular or dual chamber cardiac pacemaker, or by an external, temporary monitoring/stimulation device or by a VAD control system.

Accordingly, an embodiment of the present invention is disclosed in the context of an LVAD operating in conjunction with a multi-chamber monitoring/stimulation system provided with the capacity to collect and store pressure data and process data for determining a metric of ventricular synchronization. A ventricular assist device is generally provided for unloading a failing ventricle and assisting the ventricle's pumping function. Various types of ventricular assist devices have been proposed. Reference is made to U.S. Pat. No. 6,443,884, issued to Miyawaki, U.S. Pat. No. 5,169,381 issued to Snyders, U.S. Pat. No. 5,011,380 issued to Kovacs, U.S. Pat. No. 6,264,601 issued to Jassawalla et al., and U.S. Pat. No. 4,995,857 issued to Arnold, all of which patents are incorporated herein by reference in their entirety. Ventricular assist devices may be used acutely, for example in conjunction with a surgical procedure, or chronically, for example to sustain a patient awaiting heart transplant. It is contemplated that a patient may benefit from optimizing ventricular synchrony during acute or chronic application of a ventricular assist device.

Figure 9:
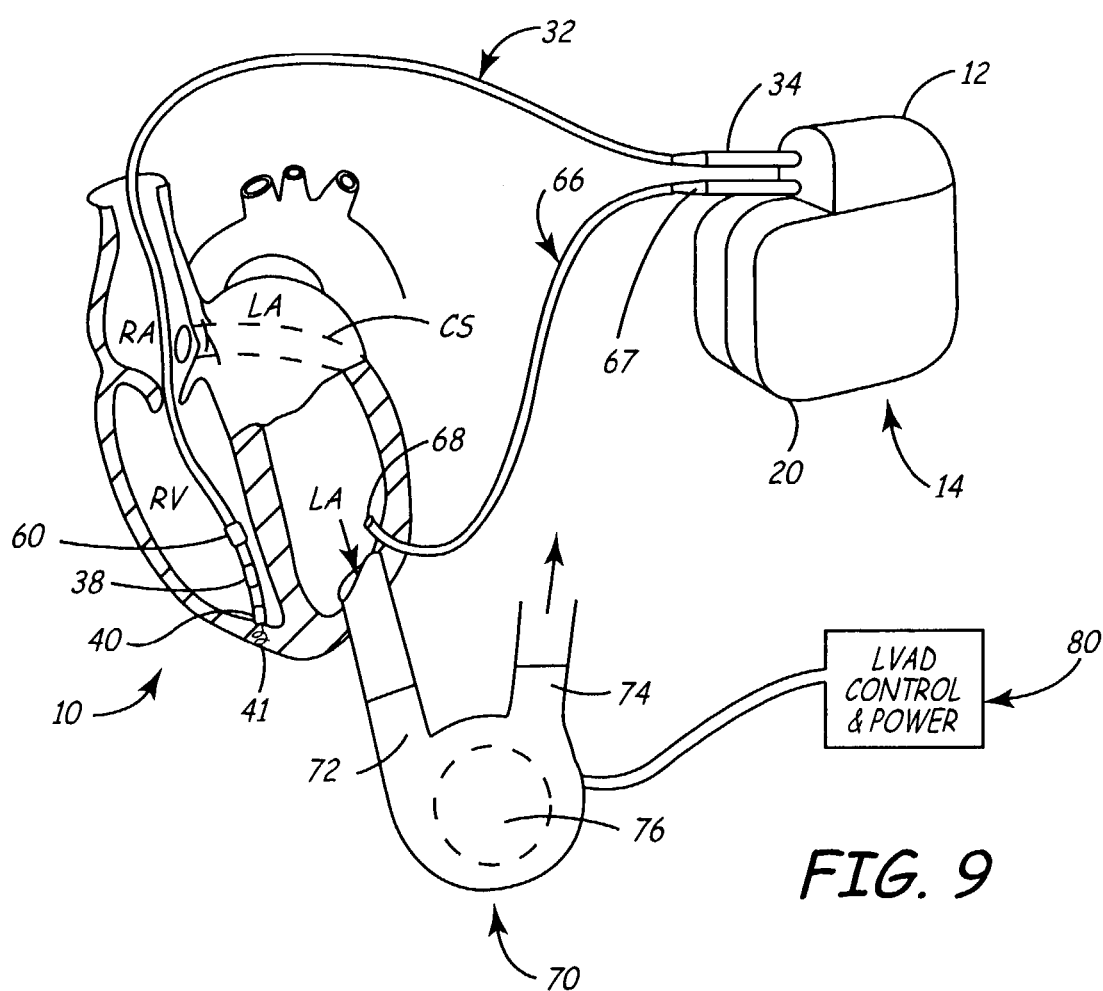
FIG. 9 is a partially cut-away view of a patient's heart coupled to a multi-chamber monitor/stimulator system via cardiac leads and additionally coupled to an LVAD.

FIG. 9 is a partially cut-away view of a patient's heart coupled to a multi-chamber monitor/stimulator system via cardiac leads and additionally coupled to an LVAD. The LVAD 70 includes an inflow conduit 72 that is surgically inserted into the apical area of the LV such that the blood volume normally filling the LV is at least partially unloaded into a central pumping chamber 76 of LVAD 70. Upon actuation, the pumping chamber 76 ejects blood through outflow conduit 74 which is coupled to the arterial system, typically to the ascending or descending aorta. Inflow and outflow conduits 72 and 74 typically include valves in order to control the direction of blood flow into and out of LVAD 70. Actuation of LVAD 70 may be pneumatic, hydraulic, electromagnetic, or by other means known in the art. LVAD control and power unit 80 provides the power required for actuating LVAD 70. Control and power unit 80 additionally controls the actuation of LVAD 70 in relation to time, pressure, flow rate or other operating factors. Control and power unit 80 may be incorporated with LVAD 70 in a fully implantable system, or control and power unit 80 may be located external to the patient's body with any necessary connections for actuating LVAD 70 provided transcutaneously.

In the embodiment shown in FIG. 9, a pressure transducer 68 is positioned in the left ventricle transmyocardially. Pressure transducer 68 is carried by a lead 66 coupled to a monitor/stimulator 14 via a connector 67. During placement of an LVAD, exposure of the LV advantageously allows an opportunity for placing a pressure sensor directly in the LV. Alternatively, a sensor may be positioned in a cardiac vein, as described previously, or elsewhere for measuring a correlate of LVP.

Other identically labeled components in FIG. 9 correspond to those in FIG. 5. IPG 14 in this embodiment receives EGM and RVP signals from lead 32 and LVP signals from lead 66. RVP and LVP signals are stored and processed in IPG 14 as described previously for detecting a metric of ventricular synchronization. IPG 14 is in telemetric communication with LVAD control and power unit 80 such that LVAD operating parameters may be adjusted according to commands received from IPG 14. Alternatively, LVAD control and power unit 80 receives pressure-related data transmitted from IPG 14 and processes such data for determining a metric of ventricular synchronization and adjusting LVAD actuation time based on that metric.

Figure 10:
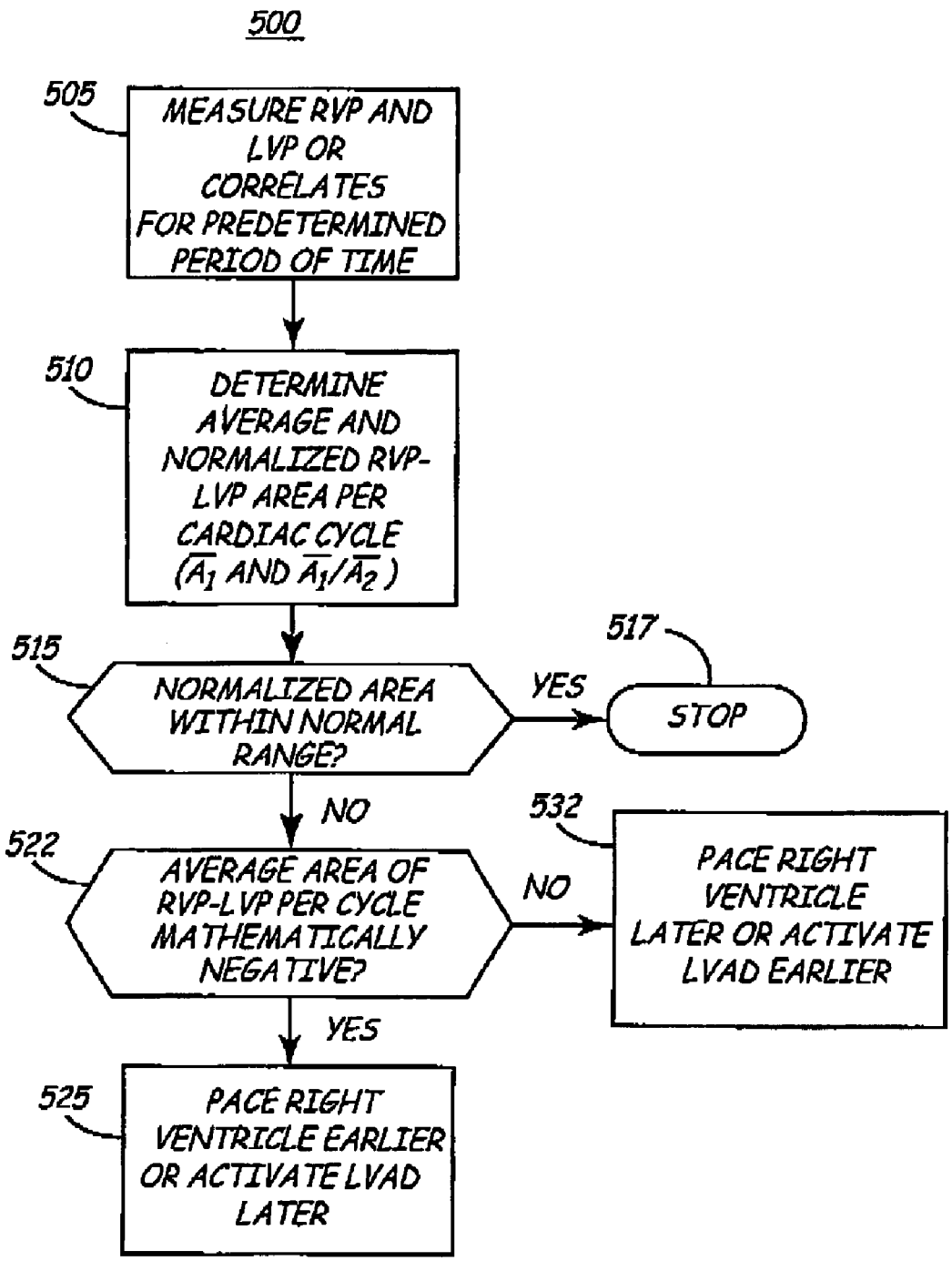
FIG. 10 is a flow chart summarizing steps included in a method for optimizing ventricular synchronization for use with a ventricular assist system of the type shown in FIG. 9.

FIG. 10 is a flow chart summarizing steps included in a method for optimizing ventricular synchronization for use with a ventricular assist system of the type shown in FIG. 9. At step 505, RVP and LVP, or correlates thereof, are simultaneously measured as described previously. At step 510, a ventricular synchronization metric is determined based on the RVP-LVP relationship. In a preferred embodiment, the average area enclosed per cardiac cycle by the RVP-LVP plot, $\overline{A}_1$, is calculated and normalized by the average area of the RVP and LVP range per cardiac cycle, $\overline{A}_2$. Either average RVP-LVP loop area, $\overline{A}_1$, or normalized RVP-LVP loop area $\overline{A}_1/\overline{A}_2$, may then be compared to a predetermined normal range associated with normal ventricular synchrony. If the metric falls at or near the expected normal value, the method 500 may be terminated at step 517. No adjustment to the current ventricular assist therapy is needed.

If the synchronization metric does not meet the normal synchronization criterion at decision step 515, the method 600 determines which ventricle is leading in pressure development. If the average area enclosed by the RVP-LVP relationship is mathematically negative as calculated at step 522, then the pressure developed in the left ventricle leads the pressure developed in the right ventricle. In this case, right ventricular pacing parameters are adjusted at step 525 to pace the right ventricle earlier in the cardiac cycle to restore more normal ventricular synchrony. Alternatively or additionally, the LVAD operating parameters may be adjusted to actuate the LVAD later in the cardiac cycle.

If the average area enclosed by the RVP-LVP relationship is mathematically positive, then the pressure developed in the left ventricle lags the pressure developed in the right ventricle. In this case, method 500 will adjust RV pacing parameters at step 532 such that the right ventricle is paced later and/or adjust LVAD operation parameters to actuate the LVAD earlier in the cardiac cycle.

Thus a method and apparatus have been described for determining a metric of ventricular synchronization and optimizing a cardiac resynchronization or ventricular assist therapy based on the synchronization metric. Improvement of ventricular synchrony is expected to provide greater benefit to the patient by enhancing ventricular pumping efficiency and allowing myocardial recovery.

While the invention has been described herein in the context of specific embodiments, it is recognized that numerous variations of these embodiments may be apparent to those skilled in the art. The descriptions provided herein, therefore, are intended to be exemplary, not limiting, with regard to the following claims.

The invention claimed is:

1. A closed loop method of improving cardiac resynchronization therapy based upon detected physiologic characteristics of a heart, comprising:
   measuring a pressure development characteristic of a first ventricle and a second ventricle and based on individual measurements of pressure development for said first ventricle and for said second ventricle during at least one cardiac cycle;
   determining whether the first ventricle or the second ventricle relatively leads pressure development and proceeding to the next step if the determination is affirmative or halting the method if the determination is negative; and
   adjusting a timing parameter of a first pacing electrode in electrical communication with the first ventricle relative to a second pacing electrode in electrical communication with the second ventricle so that pressure development in the first ventricle and the second ventricle occurs substantially at the same time.

2. A method according to claim 1, wherein measuring pressure development comprises deploying a first pressure transducer in fluid communication with the first ventricle and a second pressure transducer in fluid communication with the second ventricle.

3. A method according to claim 1, further comprising coupling the first pacing electrode to a portion of endocardial tissue of the first ventricle.

4. A method according to claim 1, further comprising coupling the second pacing electrode to a portion of endocardial tissue of the second ventricle.

5. A method according to claim 1, further comprising coupling the first pacing electrode to a portion of epicardial tissue of the first ventricle.

6. A method according to claim 1, further comprising coupling the second pacing electrode to a portion of epicardial tissue of the second ventricle.

7. A method according to claim 1, wherein the pressure development of the first ventricle is measured by a pressure transducer disposed within the first ventricle.

8. A method according to claim 1, wherein the pressure development of the second ventricle is measured by a pressure transducer disposed within the second ventricle.

9. A method according to claim 1, wherein the pressure development of the first ventricle is measured by a pressure transducer adapted to be disposed within a portion of the coronary sinus or the great cardiac vein.

10. A method according to claim 1, further comprising fluidly coupling a ventricular assist device to the first ventricle.

11. A method according to claim 10, wherein the pressure development of the first ventricle is measured by a pressure transducer coupled to the ventricle assist device.

12. A method according to claim 1, wherein the pressure development of the first ventricle is measured by a pressure transducer adapted to be coupled to a septal wall portion between the first ventricle and the second ventricle.

13. A method according to claim 1, wherein the pressure development of the first ventricle is measured by a pressure transducer adapted to pass through a septal wall portion between the first ventricle and the second ventricle.

14. A method according to claim 1, further comprising:
providing via telemetry information regarding at least a one of the following:
a pressure development characteristic of the first ventricle,
a pressure development characteristic of the second ventricle,
a pressure development characteristic of a ventricular assist device,
a pacing stimulus timing characteristic for a ventricular chamber or an atrial chamber,
a pacing stimulus interval timing characteristic for a ventricular chamber or an atrial chamber,
a withhold pacing stimulus command for a ventricular chamber,
a control sequence for a ventricular assist device.

15. A method according to claim 14, further comprising controlling a ventricular assist device based at least in part upon one of said telemetered characteristics.

16. A method according to claim 1, further comprising: chronically delivering a cardiac resynchronization therapy via the first pacing electrode and the second pacing electrode at the then-current pacing timing settings in the event that pressure development in the first ventricle and the second ventricle occurs substantially at the same time.

17. A computer readable medium for performing a method of improving cardiac resynchronization therapy based upon detected physiologic characteristics of a heart, comprising:
instructions encoded upon a computer readable medium for measuring a pressure development characteristic of a first ventricle and a second ventricle and based on individual measurements of pressure development for said first ventricle and for said second ventricle during at least one cardiac cycle;
instructions encoded upon the computer readable medium for determining whether the first ventricle or the second ventricle relatively leads pressure development and proceeding to the next step if the determination is affirmative or halting the method if the determination is negative; and
instructions encoded upon the computer readable medium for adjusting a timing parameter of a first pacing electrode in electrical communication with the first ventricle relative to a second pacing electrode in electrical communication with the second ventricle so that pressure development in the first ventricle and the second ventricle occurs substantially at the same time.

18. A medium according to claim 17, wherein the instructions encoded upon the computer readable medium for measuring pressure development comprises instructions encoded upon the computer readable medium for communicating with a first pressure transducer in fluid communication with the first ventricle and a second pressure transducer in fluid communication with the second ventricle.

19. A medium according to claim 17, wherein the pressure development of the first ventricle is measured by a pressure transducer disposed within the first ventricle.

20. A method for optimizing ventricular synchronization comprising:
measuring a right ventricular pressure and a left ventricular pressure during at least one cardiac cycle;
determining a metric of ventricular synchronization based on the relationship between the measured right ventricular pressure and the measured left ventricular pressure so that said metric compensates for the ventricle leading in pressure development during ventricular asynchrony;
comparing the metric to a predetermined criterion that distinguishes acceptable ventricular synchrony from unacceptable ventricular asynchrony; and
adjusting a therapy when the metric does not meet the criterion for acceptable ventricular synchrony.

21. An apparatus for delivering closed loop cardiac resynchronization therapy based upon detected physiologic characteristics of a heart, comprising:
means for measuring a pressure development characteristic of a first ventricle and a second ventricle and based on individual measurements of pressure development for said first ventricle and for said second ventricle during at least one cardiac cycle;
means for determining whether the first ventricle or the second ventricle relatively leads pressure development and proceeding to the next step if the determination is affirmative or halting the method if the determination is negative; and
means including a first pacing electrode and a second pacing electrode for adjusting a timing parameter of the first pacing electrode in electrical communication with the first ventricle relative to the second pacing electrode in electrical communication with the second ventricle so that pressure development in the first ventricle and the second ventricle occurs substantially at the same time.

22. An apparatus according to claim 21, wherein the means for measuring pressure development includes means for deploying a first pressure transducer in fluid communication with the first ventricle and a second pressure transducer in fluid communication with the second ventricle.

23. An apparatus according to claim 21, wherein the first pacing electrode is adapted to be coupled to a portion of endocardial tissue of the first ventricle.

24. An apparatus according to claim 21, wherein the second pacing electrode is adapted to be coupled to a portion of endocardial tissue of the second ventricle.

25. An apparatus according to claim 21, wherein the first pacing electrode is adapted to be coupled to a portion of epicardial tissue of the first ventricle.

26. An apparatus according to claim 21, wherein the second pacing electrode is adapted to be coupled to a portion of epicardial tissue of the second ventricle.

27. An apparatus according to claim 21, wherein the means for measuring comprises a pressure transducer adapted to be disposed within the first ventricle.

* * * * *